United States Patent
Mos et al.

(10) Patent No.: US 7,619,737 B2
(45) Date of Patent: Nov. 17, 2009

(54) METHOD OF MEASUREMENT, AN INSPECTION APPARATUS AND A LITHOGRAPHIC APPARATUS

(75) Inventors: Everhardus Cornelis Mos, Best (NL); Maurits Van Der Schaar, Eindhoven (NL)

(73) Assignee: ASML Netherlands B.V, Veldhoven (NL)

( * ) Notice: Subject to any disclaimer, the term of this patent is extended or adjusted under 35 U.S.C. 154(b) by 377 days.

(21) Appl. No.: 11/656,004

(22) Filed: Jan. 22, 2007

(65) Prior Publication Data
US 2008/0174753 A1    Jul. 24, 2008

(51) Int. Cl.
*G01B 11/00* (2006.01)

(52) U.S. Cl. ...................... 356/401; 356/620
(58) Field of Classification Search .......... 356/600, 356/625, 630, 401, 620
See application file for complete search history.

(56) References Cited

U.S. PATENT DOCUMENTS

| | | | |
|---|---|---|---|
| 5,703,692 A | 12/1997 | McNeil et al. | 356/445 |
| 5,880,838 A | 3/1999 | Marx et al. | 356/351 |
| 5,963,329 A | 10/1999 | Conrad et al. | 356/372 |
| 6,608,690 B2 | 8/2003 | Niu et al. | 356/635 |
| 6,699,624 B2 | 3/2004 | Niu et al. | 430/5 |
| 6,704,661 B1 | 3/2004 | Opsal et al. | 702/27 |
| 6,721,691 B2 | 4/2004 | Bao et al. | 702/189 |
| 6,738,138 B2 | 5/2004 | Wei | 356/369 |
| 6,753,961 B1 | 6/2004 | Norton et al. | 356/364 |
| 6,768,983 B1 | 7/2004 | Jakatdar et al. | 706/46 |
| 6,772,084 B2 | 8/2004 | Bischoff et al. | 702/127 |
| 6,785,638 B2 | 8/2004 | Niu et al. | 702/189 |
| 6,813,034 B2 | 11/2004 | Rosencwaig et al. | 356/601 |
| 6,819,426 B2 | 11/2004 | Sezginer et al. | 356/401 |
| 6,856,408 B2 | 2/2005 | Raymond | 356/601 |
| 6,919,964 B2 | 7/2005 | Chu | 356/601 |
| 6,928,628 B2 | 8/2005 | Seligson et al. | 716/4 |
| 6,972,852 B2 | 12/2005 | Opsal et al. | 356/625 |
| 6,974,962 B2 | 12/2005 | Brill et al. | 250/548 |
| 6,987,572 B2 | 1/2006 | Lakkapragada et al. | 356/601 |
| 7,046,376 B2 | 5/2006 | Sezginer | 356/601 |
| 7,061,615 B1 | 6/2006 | Lowe-Webb | 356/401 |
| 7,061,623 B2 | 6/2006 | Davidson | 356/497 |
| 7,061,627 B2 | 6/2006 | Opsal et al. | 356/601 |
| 7,068,363 B2 | 6/2006 | Bevis et al. | 356/237.5 |
| 7,277,172 B2 * | 10/2007 | Kandel et al. | 356/369 |
| 7,379,184 B2 * | 5/2008 | Smith et al. | 356/401 |
| 2004/0119970 A1 | 6/2004 | Dusa et al. | 356/237.1 |
| 2006/0033921 A1 | 2/2006 | Den Boef et al. | 356/446 |
| 2006/0066855 A1 | 3/2006 | Den Boef et al. | 356/401 |
| 2006/0115751 A1 * | 6/2006 | Fay et al. | 430/22 |
| 2006/0126074 A1 | 6/2006 | Van Der Werf et al. | 356/489 |
| 2006/0139592 A1 | 6/2006 | Den Boef et al. | 355/53 |
| 2006/0256324 A1 | 11/2006 | Den Boef et al. | 356/237.2 |
| 2007/0003849 A1 | 1/2007 | Shirai | 430/57.7 |

\* cited by examiner

*Primary Examiner*—L. G Lauchman
(74) *Attorney, Agent, or Firm*—Sterne, Kessler, Goldstein & Fox P.L.L.C.

(57) ABSTRACT

Radiation is projected onto a plurality of targets on a substrate. By assuming that the overlay error derivable from asymmetry varies smoothly across the substrate, the number of targets measured can be reduced. This may result in a smaller area of the scribe lane being used by targets for each layer of the substrate.

16 Claims, 3 Drawing Sheets

METHOD OF MEASUREMENT, AN INSPECTION APPARATUS AND A LITHOGRAPHIC APPARATUS

FIELD

The present invention relates to a method of inspection usable, for example, in the manufacture of a device by a lithographic technique and to a method of manufacturing a device using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, one or more parameters of the patterned substrate are typically measured, for example the overlay error between successive layers formed in or on the substrate. There are various techniques for making measurements of the microscopic structures formed in a lithographic process, including the use of a scanning electron microscope and various specialized tools. One form of specialized inspection tool is a scatterometer in which a beam of radiation is directed onto a target on the surface of the substrate and one or more properties of the scattered or reflected beam are measured. By comparing one or more properties of the beam before and after it has been reflected or scattered by the substrate, one or more properties of the substrate may be determined. This may be done, for example, by comparing the reflected beam with data stored in a library of known measurements associated with a known substrate property. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity of the scattered radiation as a function of angle. An ellipsometer measures polarization state.

Such a system of illuminating a target and collecting data from the reflected radiation is often used to calculate the overlay error for a pattern. Generally this is achieved by etching a plurality of superimposed gratings (forming a target) into the substrate and measuring the overlay error between the gratings. However, there are many different parameters such as linear displacement, rotation, magnification and/or asymmetry. To account for these different factors, the reflected radiation has been measured from a large number of different positions and a large number of superimposed patterns (or gratings) have been used. Each of these targets occupies an area on the substrate that could otherwise be used for other patterns, such as those that form the basis for an integrated circuit.

The targets are generally positioned in dedicated scribe lanes on the substrate. Each time a new pattern is etched into the substrate a new set of targets is etched to ascertain the overlay error between the present pattern and the immediately preceding pattern. Substrates can have many patterned layers so although one set of targets may not fill a scribe lane many sets of targets are used in the manufacture of an integrated circuit.

SUMMARY

It is desirable, for example, to provide an alternative method of calculating the overlay error in which less area of the substrate is required.

According to an aspect of the invention, there is provided a method of measuring an overlay error in a substrate, the method comprising:

projecting a beam of radiation onto a plurality of targets at a plurality of positions on the substrate;

measuring radiation reflected from each of the plurality of targets on the substrate using a scatterometer; and detecting and calculating an extent of the overlay error from the reflected radiation, wherein the calculation assumes that a proportion of the overlay error in each target deriving from asymmetry of the targets is constant for the plurality of positions.

According to a further aspect of the invention, there is provided an inspection apparatus configured to measure a property of a substrate, the apparatus comprising:

a radiation projector configured to project radiation onto a plurality of targets at a plurality of positions on the substrate;

a detector configured to detect radiation reflected from each of the targets; and a data handling unit configured to calculate overlay error on the basis of the radiation reflected from the plurality of targets assuming that the overlay error deriving from the asymmetry of the targets is constant for the plurality of targets.

According to a further aspect of the invention, there is provided a method of measuring an overlay error in a substrate, the method comprising:

projecting a beam of radiation onto a plurality of targets at a plurality of positions on the substrate;

measuring radiation reflected from each of the plurality of targets on the substrate using a scatterometer; and detecting and calculating an extent of the overlay error from the reflected radiation, wherein the calculation assumes that a proportion of the overlay error in each target deriving from a parameter is constant for the plurality of positions.

According to a further aspect of the invention, there is provided an inspection apparatus configured to measure a property of a substrate, the apparatus comprising:

a radiation projector configured to project radiation onto a plurality of targets at a plurality of positions on the substrate;

a detector configured to detect radiation reflected from each of the targets; and a data handling unit configured to calculate overlay error on the basis of the radiation reflected from the plurality of targets assuming that the overlay error deriving from a parameter is constant for the plurality of targets.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
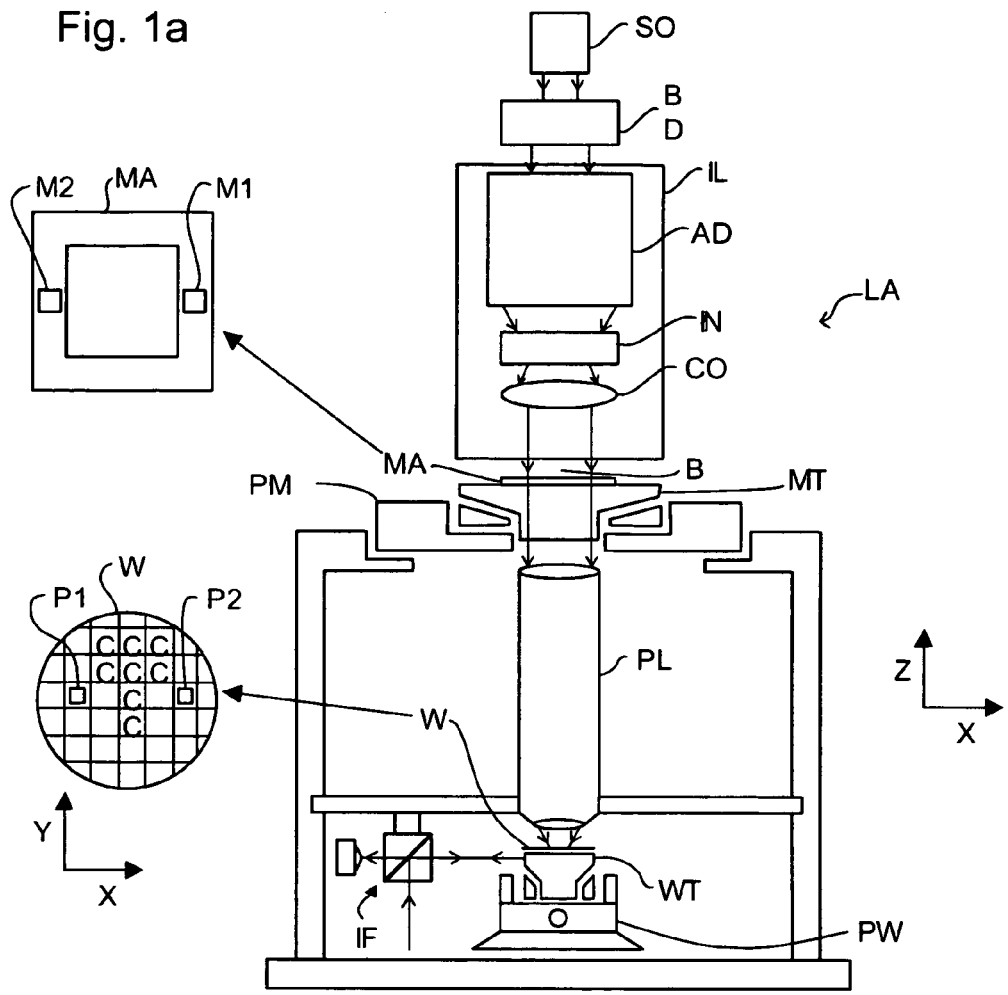
FIG. 1a depicts a lithographic apparatus.

FIG. 1a schematically depicts a lithographic apparatus. The apparatus comprises:

- an illumination system (illuminator) IL configured to condition a radiation beam B (e.g. UV radiation or EUV radiation);
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g. a resist-coated wafer) W and connected to a second positioner PW configured to accurately position the substrate in accordance with certain parameters; and
- a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more support structures). In such "multiple stage" machines the additional tables and/or support structures may be used in parallel, or preparatory steps may be carried out on one or more tables and/or support structures while one or more other tables and/or support structures are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
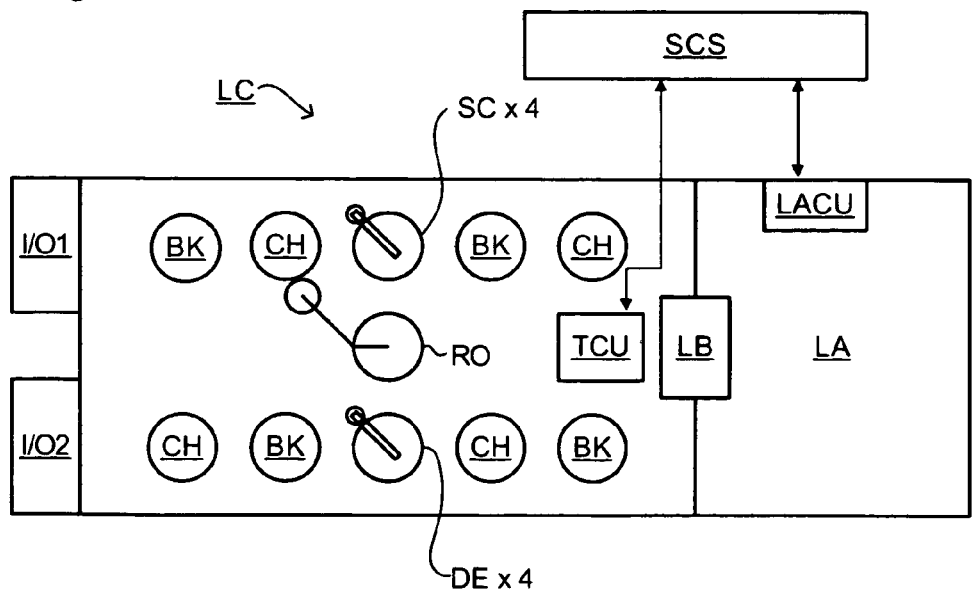
FIG. 1b depicts a lithographic cell or cluster.

As shown in FIG. 1b, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

Figure 2:
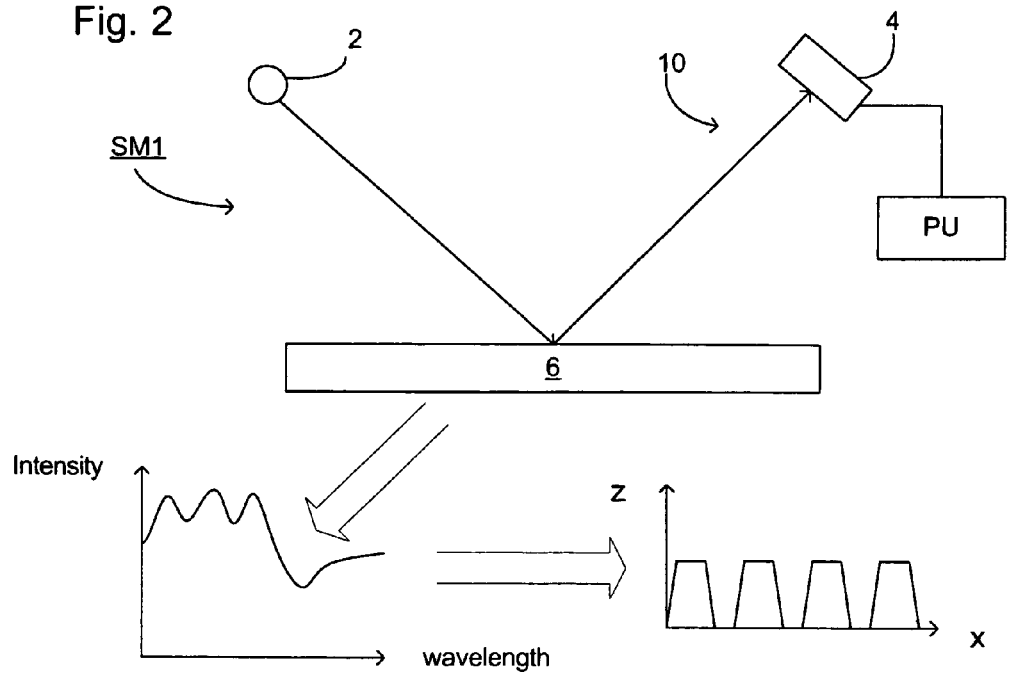
FIG. 2 depicts a first scatterometer.

FIG. 2 depicts a scatterometer SM1 which may be used in an embodiment of the invention. It comprises a broadband (white light) radiation projector 2 which projects radiation onto a substrate W. The reflected radiation is passed to a spectrometer detector 4, which measures a spectrum 10 (i.e. a measurement of intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 2. In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
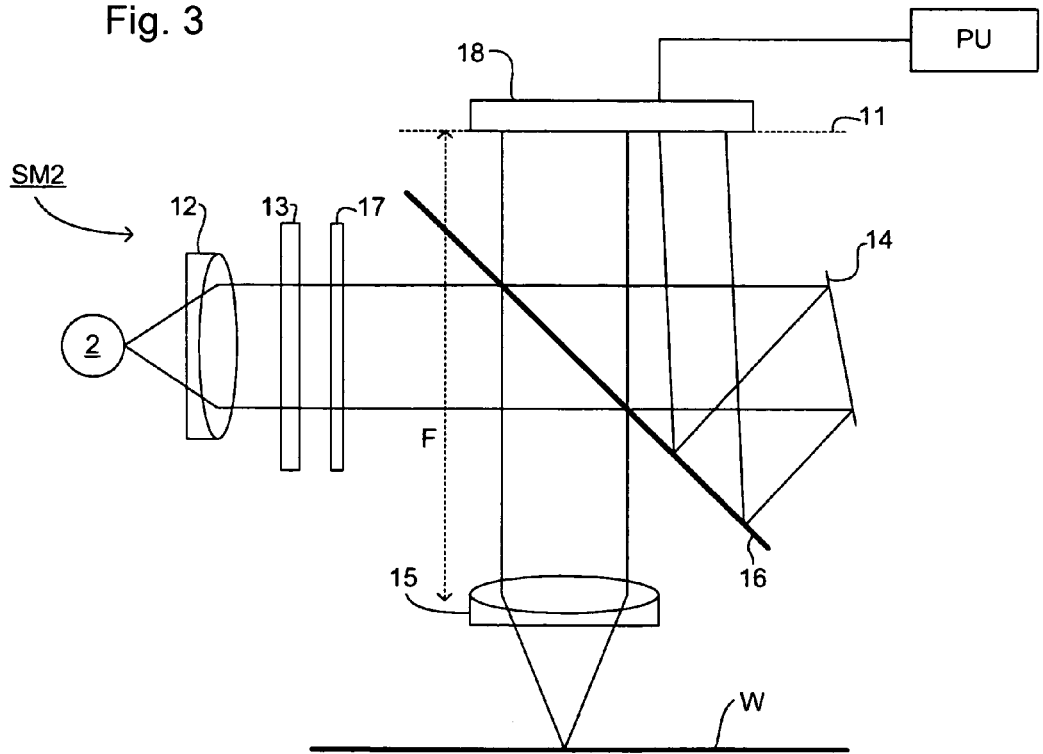
FIG. 3 depicts a second scatterometer.

Another scatterometer SM2 that may be used with an embodiment of the invention is shown in FIG. 3. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), desirably at least 0.9 or at least 0.95. An immersion scatterometer may even have a lens with a numerical aperture over 1. The reflected radiation then transmits through partially reflective surface 16 into a detector 18 in order to have the scatter spectrum detected. The detector may be located in the back-projected pupil plane 11, which is at the focal length of the lens 15, however the pupil plane may instead be re-imaged with auxiliary optics (not shown) onto the detector 18. The pupil plane is the plane in which the radial position of radiation defines the angle of incidence and the angular position defines the azimuth angle of the radiation. The detector is desirably a two-dimensional detector so that a two-dimensional angular scatter spectrum (i.e. a measurement of intensity as a function of angle of scatter) of the substrate target can be measured. The detector 18 may be, for example, an array of CCD or CMOS sensors, and may have an integration time of, for example, 40 milliseconds per frame.

A reference beam is often used, for example, to measure the intensity of the incident radiation. To do this, when the radiation beam is incident on the partially reflective surface 16 part of it is transmitted through the surface as a reference beam towards a reference mirror 14. The reference beam is then projected onto a different part of the same detector 18.

One or more interference filters 13 are available to select a wavelength of interest in the range of, say, 405-790 nm or even lower, such as 200-300 nm. The interference filters may be tunable rather than comprising a set of different filters. A grating could be used instead of or in addition to one or more interference filters.

The detector 18 may measure the intensity of scattered light at a single wavelength (or narrow wavelength range), the intensity separately at multiple wavelengths or the intensity integrated over a wavelength range. Further, the detector may separately measure the intensity of transverse magnetic— (TM) and transverse electric—(TE) polarized radiation and/or the phase difference between the transverse magnetic- and transverse electric-polarized radiation.

Using a broadband radiation source 2 (i.e. one with a wide range of radiation frequencies or wavelengths—and therefore of colors) is possible, which gives a large etendue, allowing the mixing of multiple wavelengths. The plurality of wavelengths in the broadband desirably each has a bandwidth of $\delta\lambda$ and a spacing of at least $2\delta\lambda$ (i.e. twice the wavelength bandwidth). Several "sources" of radiation may be different portions of an extended radiation source which have been split using, e.g., fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in U.S. patent application publication no. US 2006-0066855, which document is hereby incorporated in its entirety by reference.

The target on substrate W may be a grating which is printed such that after development, the bars are formed of solid resist lines. The bars may alternatively be etched into the substrate. The target pattern is chosen to be sensitive to a parameter of interest, such as focus, dose, overlay, chromatic aberration in the lithographic projection apparatus, etc., such that variation in the relevant parameter will manifest as variation in the printed target. For example, the target pattern may be sensitive to chromatic aberration in the lithographic projection apparatus, particularly the projection system PL, and illumination symmetry and the presence of such aberration will manifest itself in a variation in the printed target pattern. Accordingly, the scatterometry data of the printed target pattern is used to reconstruct the target pattern. The parameters of the target pattern, such as line width and shape, may be input to the reconstruction process, performed by a processing unit PU, from knowledge of the printing step and/or other scatterometry processes.

Figure 4:
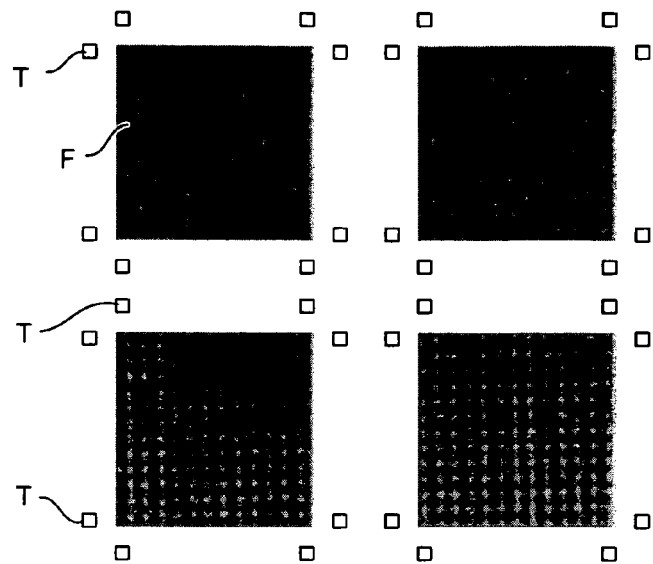
FIG. 4 depicts an arrangement of targets on a substrate according to an embodiment of the invention.
Figure 5:
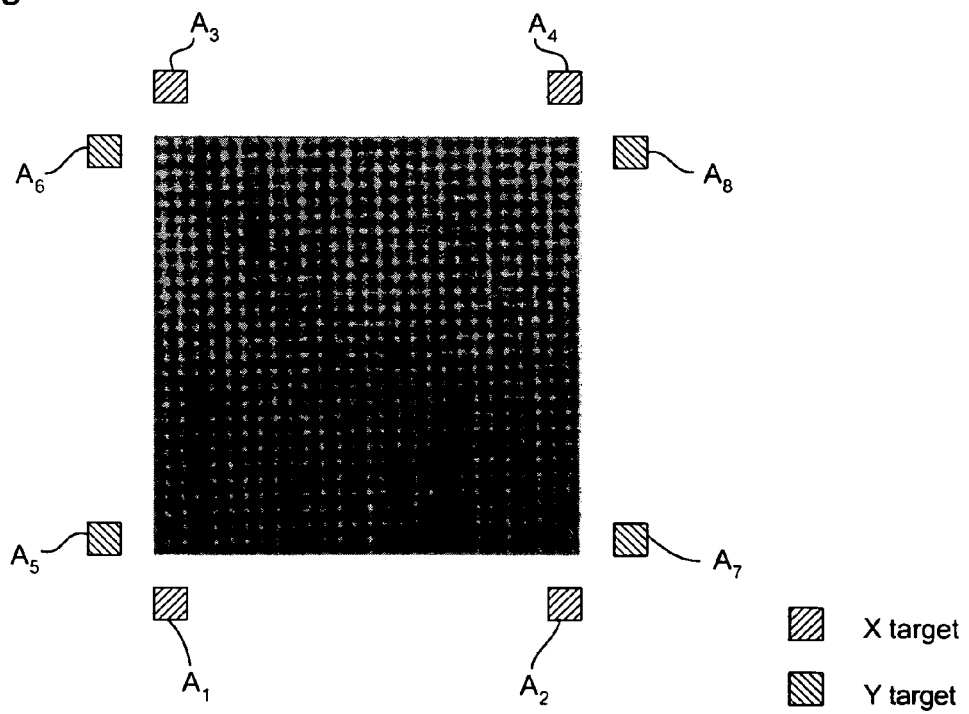
FIG. 5 depicts a detailed view of an arrangement of targets according to an embodiment of the invention.

As can be seen in FIGS. 4 and 5, there are a plurality of targets T, A arranged around each field F. A number of different parameters such as magnification M, rotation R and displacement T affect the overlay error and each of these may be incorporated into a model for calculating the overlay error. Furthermore, one or more of the parameters may vary within the field (intrafield) and one or more parameters may vary both within the field and between fields (interfield). The following parameters are generally incorporated into a model for calculating the overlay error:

Interfield: Mx, My, Rx, Ry

Intrafield: Tx, Ty, Mx, My, Rx, Ry where M is the magnification, R is the rotation and T is the displacement.

Furthermore, the overlay error will be proportional to the asymmetry between the +1st and −1st order in the measured spectrum of two overlaying targets A. According to an embodiment, the proportionality, K, of the overlay with respect to the measured asymmetry is assumed to vary smoothly across the substrate W and can be assumed to be constant within each field. Using this assumption there is an additional intrafield parameter so that the parameters are as follows:

Interfield: Mx, My, Rx, Ry

Intrafield: Tx, Ty, Mx, My, Rx, Ry, K

Thus the total number of parameters for N fields is 7N+4, and only 8 measurements (i.e. 8 targets) are necessary. If $dX_1$ is the measured overlay error at a position X, Y, then $$dX_1 = T_x M_x X_1 - R_x Y_1$$

where $$dX_1 = \left(\frac{A_x}{K}\right) - d,$$

wherein d is a predetermined bias distance between two overlaying targets A in two respective layers.

Thus the model results in the following matrix:

$$\begin{pmatrix} 1 & x_1^f & -y_1^f & d_1 & 0 & 0 & 0 & 0 \\ 1 & x_2^f & -y_2^f & d_2 & 0 & 0 & 0 & 0 \\ 1 & x_3^f & -y_3^f & d_3 & 0 & 0 & 0 & 0 \\ 1 & x_4^f & -y_4^f & d_4 & 0 & 0 & 0 & 0 \\ 0 & 0 & 0 & 0 & 1 & y_5^f & x_5^f & d_5 \\ 0 & 0 & 0 & 0 & 1 & y_6^f & x_6^f & d_6 \\ 0 & 0 & 0 & 0 & 1 & y_7^f & x_7^f & d_7 \\ 0 & 0 & 0 & 0 & 1 & y_8^f & x_8^f & d_8 \end{pmatrix} \begin{pmatrix} K_x T_x \\ K_x M_x \\ K_x R_x \\ K_x \\ K_y T_y \\ K_y M_y \\ K_y R_y \\ K_y \end{pmatrix} = \begin{pmatrix} A_1^x \\ A_2^x \\ A_3^x \\ A_4^x \\ A_5^y \\ A_6^y \\ A_7^y \\ A_8^y \end{pmatrix}$$

wherein the superscript f represent the field reference with respect to the substrate. The matrix can be solved by matrix inversion. $K_x$ and $K_x$ should be equal, but can be solved separately and can be used as a parity check.

According to an embodiment, only 8 targets in each of the two subsequent layers are therefore needed instead of the, for example, 20 targets needed for a conventional method. This results in less scribe lane usage and a larger usable area of the substrate. Indeed if each target is 40 μm×40 μm, scribe lane usage is reduced to 40 μm*8=320 μm. This method may be further improved by using a 2 dimensional target (e.g., a 2D grating) which would result in only 4 targets being needed.

An embodiment of the invention is not limited to just the intrafield parameters and can could equally be applied to the interfield parameters and asymmetry values for each of the pixels of the corresponding $+1^{st}$ and the $-1^{st}$ order of the measured spectra of the eight targets.

In an embodiment, the radiation beam projected onto the targets is linearly polarized.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of measuring an overlay error in a substrate, the method comprising:
    projecting a beam of radiation onto a plurality of targets at a plurality of positions on the substrate;
    measuring radiation reflected from each of the plurality of targets on the substrate using a scatterometer; and
    determining, using a processing unit, an extent of the overlay error from the reflected radiation assuming that a proportionality of the overlay error in each target with respect to an asymmetry of the targets is constant for the plurality of positions.

2. The method of claim 1, wherein the measured reflected radiation is reflected from eight positions on the substrate.

3. The method of claim 1, wherein each of the targets is a 2D grating and the measured reflected radiation is reflected from four points on the substrate.

4. The method of claim 1, wherein the beam is linearly polarized.

5. The method of claim 1, wherein the measured reflected radiation is reflected from eight targets, $A_1, A_2, A_3, A_4, A_5, A_6, A_7, A_8$, and the overlay error is calculated by solving the following equation:

$$\begin{pmatrix} 1 & x_1^f & -y_1^f & d_1 & 0 & 0 & 0 & 0 \\ 1 & x_2^f & -y_2^f & d_2 & 0 & 0 & 0 & 0 \\ 1 & x_3^f & -y_3^f & d_3 & 0 & 0 & 0 & 0 \\ 1 & x_4^f & -y_4^f & d_4 & 0 & 0 & 0 & 0 \\ 0 & 0 & 0 & 0 & 1 & y_5^f & x_5^f & d_5 \\ 0 & 0 & 0 & 0 & 1 & y_6^f & x_6^f & d_6 \\ 0 & 0 & 0 & 0 & 1 & y_7^f & x_7^f & d_7 \\ 0 & 0 & 0 & 0 & 1 & y_8^f & x_8^f & d_8 \end{pmatrix} \begin{pmatrix} K_x T_x \\ K_x M_x \\ K_x R_x \\ K_x \\ K_y T_y \\ K_y M_y \\ K_y R_y \\ K_y \end{pmatrix} = \begin{pmatrix} A_1^x \\ A_2^x \\ A_3^x \\ A_4^x \\ A_5^y \\ A_6^y \\ A_7^y \\ A_8^y \end{pmatrix}$$

where T represents the displacement, M represents the magnification, R represents the rotation, K is the proportion of overlay error with respect to the asymmetry, superscript f represent the field reference with respect to the substrate, d represents a bias distance between two overlaying targets A in two respective layers, and X, Y represent respective orthogonal positions.

6. The method of claim 1, wherein each target comprises a plurality of superimposed gratings.

7. A method of manufacturing a substrate comprising projecting a patterned beam of radiation onto the substrate to expose the substrate wherein the exposing is based on overlay error determined by the method of claim 1.

8. An inspection apparatus configured to measure a property of a substrate, the apparatus comprising:
a radiation projector configured to project radiation onto a plurality of targets at a plurality of positions on the substrate;
a detector configured to detect radiation reflected from each of the targets; and
a data handling unit configured to calculate overlay error on the basis of the radiation reflected from the plurality of targets assuming that the overlay error with respect to an asymmetry of the targets is constant for the plurality of targets.

9. The apparatus of claim 8, wherein the detected reflected radiation is reflected from eight targets on the substrate.

10. The apparatus of claim 8, wherein each of the targets is a 2D grating and the detected reflected radiation is reflected from four targets on the substrate.

11. The apparatus of claim 8, wherein the radiation is linearly polarized.

12. The apparatus of claim 8, wherein the detected reflected radiation is reflected from eight targets, $A_1, A_2, A_3, A_4, A_5, A_6, A_7, A_8$, and the overlay error is calculated by solving the following equation:

$$\begin{pmatrix} 1 & x_1^f & -y_1^f & d_1 & 0 & 0 & 0 & 0 \\ 1 & x_2^f & -y_2^f & d_2 & 0 & 0 & 0 & 0 \\ 1 & x_3^f & -y_3^f & d_3 & 0 & 0 & 0 & 0 \\ 1 & x_4^f & -y_4^f & d_4 & 0 & 0 & 0 & 0 \\ 0 & 0 & 0 & 0 & 1 & y_5^f & x_5^f & d_5 \\ 0 & 0 & 0 & 0 & 1 & y_6^f & x_6^f & d_6 \\ 0 & 0 & 0 & 0 & 1 & y_7^f & x_7^f & d_7 \\ 0 & 0 & 0 & 0 & 1 & y_8^f & x_8^f & d_8 \end{pmatrix} \begin{pmatrix} K_x T_x \\ K_x M_x \\ K_x R_x \\ K_x \\ K_y T_y \\ K_y M_y \\ K_y R_y \\ K_y \end{pmatrix} = \begin{pmatrix} A_1^x \\ A_2^x \\ A_3^x \\ A_4^x \\ A_5^y \\ A_6^y \\ A_7^y \\ A_8^y \end{pmatrix}$$

where T represents the displacement, M represents the magnification, R represents the rotation, K is the proportion of overlay error with respect to the asymmetry, superscript f represent the field reference with respect to the substrate, d represents a bias distance between two overlaying targets A in two respective layers, and X, Y represent respective orthogonal positions.

13. The apparatus of claim 8, wherein each target comprises a plurality of superimposed gratings.

14. A lithographic apparatus comprising:
an illumination support configured to condition a radiation beam;
a support constructed to support a patterning device, the patterning device being capable of imparting the radiation beam with a pattern in its cross-section to form a patterned radiation beam;
a substrate table constructed to hold a substrate
a projection system configured to project the patterned radiation beam onto a target portion of the substrate; and
an inspection apparatus configured to measure a property of a substrate, the apparatus comprising:
a detector configured to detect radiation reflected from each of a plurality of targets at a plurality of positions on a substrate; and
a data handling unit configured to calculate overlay error on the basis of the radiation reflected from the plurality of targets assuming that the overlay error with respect to an asymmetry of the targets is constant for the plurality of targets.

15. A method of measuring an overlay error in a substrate, the method comprising:
projecting a beam of radiation onto a plurality of targets at a plurality of positions on the substrate;
measuring radiation reflected from each of the plurality of targets on the substrate using a scatterometer; and
determining, using a processing unit, an extent of the overlay error from the reflected radiation assuming that a proportionality of the overlay error in each target with respect to a parameter is constant for the plurality of positions.

16. An inspection apparatus configured to measure a property of a substrate, the apparatus comprising:
a radiation projector configured to project radiation onto a plurality of targets at a plurality of positions on the substrate;
a detector configured to detect radiation reflected from each of the targets; and
a data handling unit configured to calculate overlay error on the basis of the radiation reflected from the plurality of targets assuming that the overlay error with respect to a parameter is constant for the plurality of targets.

* * * * *